United States Patent [19]
Shimada et al.

[11] Patent Number: 5,626,837
[45] Date of Patent: May 6, 1997

[54] ORAL COMPOSITION

[75] Inventors: Toshiya Shimada, Tokyo; Kazuo Mukasa, Konosu; Tetsuo Gomi, Tokyo; Takao Yokoo, Kasubake, all of Japan

[73] Assignee: Lion Corporation, Tokyo, Japan

[21] Appl. No.: 601,831

[22] Filed: Feb. 15, 1996

Related U.S. Application Data

[62] Division of Ser. No. 284,212, Aug. 2, 1994, abandoned.

[30] Foreign Application Priority Data

Aug. 12, 1993 [JP] Japan ..................... 5-220646

[51] Int. Cl.$^6$ .................. A61K 7/16; A61K 7/18; A61K 7/22
[52] U.S. Cl. .................. 424/49; 424/52; 424/54; 424/58
[58] Field of Search .................. 424/49–58

[56] References Cited

U.S. PATENT DOCUMENTS

| | | | |
|---|---|---|---|
| 3,472,835 | 10/1969 | Buckler et al. | 260/209 |
| 4,024,223 | 5/1977 | Noda et al. | 424/180 |
| 4,267,166 | 5/1981 | Yajima | 424/48 |
| 4,727,064 | 2/1988 | Pitha | 514/58 |
| 4,774,329 | 9/1988 | Friedman | 536/103 |
| 4,906,488 | 3/1990 | Pera | 426/573 |
| 5,139,687 | 8/1992 | Borgher et al. | 252/8.6 |
| 5,206,025 | 4/1993 | Courtelle et al. | 424/439 |
| 5,246,611 | 9/1993 | Trinh | 252/8.6 |
| 5,302,373 | 4/1994 | Giacin et al. | 424/49 |
| 5,330,749 | 7/1994 | Giacin et al. | 424/49 |

FOREIGN PATENT DOCUMENTS

| | | |
|---|---|---|
| 306455 | 3/1989 | European Pat. Off. . |
| 340171 | 11/1989 | European Pat. Off. . |
| 54-70443 | 6/1979 | Japan . |
| 59-163307 | 9/1984 | Japan . |
| 60-149530 | 8/1985 | Japan . |
| 1190623 | 7/1989 | Japan . |
| 5-931 | 1/1993 | Japan . |
| 92/00725 | 1/1992 | WIPO . |

OTHER PUBLICATIONS

Sunstap JP 01190623A2 Jul. 31, 1989 (Mouthwash Menthol Cyclodextrins).

Coku Kazuo JP 59163307A2 Sep. 14, 1984 (Breath Deodorant Peppermint Oil Cyclodextrins).

Takeda JP 60149530A Aug. 7, 1985 (Oral Chlorhexidine–Cyclodextrin Solns).

Sunstar–Hamigaki JP54070443A Jun. 6, 1974 (Ethanol Solvent Extract of Oleophilic Essence Emusified with Non–Ionic Surfactant in Dentierins).

*Primary Examiner*—Shep K. Rose
*Attorney, Agent, or Firm*—Birch, Stewart, Kolasch & Birch, LLP

[57] ABSTRACT

In an oral composition comprising a cationic bactericide, either one or both of cyclodextrin and a water-soluble flavor obtained by extracting an oil-soluble flavor with an aqueous ethanol solution are blended. The composition allows the cationic bactericide to exert its activity to a full extent, presents a pleasant feel on use without any peculiar taste, and is stable during storage. The invention eliminates the use of anionic and nonionic surfactants.

6 Claims, No Drawings

ORAL COMPOSITION

This application is a divisional of application Ser. No. 08/284,212, filed on Aug. 2, 1994, now abandoned.

BACKGROUND OF THE INVENTION

1. Field of the Invention

This invention relates to an oral composition which allows a cationic bactericide to exert its activity to a full extent, presents no peculiar taste, and is pleasant to use and stable during storage.

2. Prior Art

In the conventional oral compositions, flavors are frequently blended for the purposes of masking peculiar tastes inherent to base ingredients and effective ingredients and improving the feel on use. When a component having a strong peculiar taste, especially, a cationic bactericide having strong bitterness is blended, an oil-soluble flavor is used from the standpoint of titer.

When an oil-soluble flavor is blended in an oral preparation, in turn, an anionic or nonionic surfactant is generally added as a solubilizing agent, which will undesirably deactivate the cationic bactericide. The loss of bactericidal activity can be avoided by blending an excess amount of the cationic bactericide, which will give rise to other problems including harmfullness, storage instability and difficult bitterness masking. In addition, the anionic or nonionic surfactant itself induces mucosa stripping, stimulation and a peculiar taste to the mouth, which will, in turn, cause inconvenience like a change of taste of food and an unpleasant feel on use. For these reasons, a cationic bactericide is conventionally blended in an oral composition at the sacrifice of storage stability, peculiar taste masking, and/or optimum content.

Japanese Patent Application Kokai (JP-A) No. 70443/1979 proposes to use an oil-soluble flavor in essence form in dentifrice compositions for the purposes of masking a peculiar taste and improving the feel on use. This attempt also requires the presence of the above-mentioned surfactant which can lower the activity of a cationic bactericide. JP-A 931/1993 discloses taste improvement by the selected use of a quaternary ammonium salt among cationic bactericides. This method is effective only in the limited range and not applicable to a wide range of use.

Therefore, for oral compositions having cationic bactericides blended therein, there is a need for improvements including high activity of cationic bactericides in a wide range, elimination of a peculiar taste, a pleasant feel on use, and storage stability.

SUMMARY OF THE INVENTION

An object of the present invention is to provide a novel and improved oral composition containing a cationic bactericide which allows the cationic bactericide to exerts its activity to a full extent, presents no peculiar taste, and is pleasant to use and stable during storage.

The inventors have succeeded in avoiding the use of anionic and nonionic surfactants in an oral composition containing a cationic bactericide by blending either cyclodextrin or a water-soluble flavor obtained by extracting an oil-soluble flavor with an aqueous ethanol solution or both in the oral composition. Particularly when cyclodextrin is used, an oil-soluble flavor is solubilized as such. The resulting oral composition allows the cationic bactericide to exerts its activity to a full extent, presents no peculiar taste because of masking of a peculiar taste inherent to the cationic bactericide, is thus pleasant to use, remains stable during storage, and will find widespread use.

According to the present invention, there is provided an oral composition comprising a cationic bactericide and at least one of cyclodextrin and a water-soluble flavor obtained by extracting an oil-soluble flavor with an aqueous ethanol solution. The composition is free of anionic and nonionic surfactants.

DETAILED DESCRIPTION OF THE INVENTION

The oral composition of the invention is prepared as liquid mouth refreshers or gargles such as mouthwash, dental rinse and mouth spray, solid mouth refreshers such as troche, dentifrices such as toothpaste, wet toothpowder, toothpowder, and liquid dentifrice, chewing gum, oral paste and the like. It contains a cationic bactericide as an active ingredient and one or both of cyclodextrin and a water-soluble flavor obtained by extracting an oil-soluble flavor with an aqueous ethanol solution.

The cationic bactericides which can be used herein include (1) quaternary ammonium salt type bactericides such as alkyl pyridinium salts (e.g., benzethonium chloride, cetyl pyridinium chloride and benzalkonium chloride) and mono-long-chain-alkyl tri-short-chain-alkyl ammonium salts (e.g., cetyltrimethylammonium chloride), (2) amidines which are substituted guanidines, such as chlorhexidine and alexidine and salts thereof, (3) hexethidines which are amino-hexehydro-pyrimidine derivatives and salts thereof, and (4) amino acid series cationic surfactants such as N-α-cocoyl-L-alginine ethyl ester DL-pyrollidone carboxylic acid and salts thereof, alone or in admixture of two or more.

Preferably the cationic bactericide is blended in an amount of about 0.005 to about 0.2% by weight, more preferably about 0.01 to about 0.1% by weight of the entire composition. Less than 0.005% of the cationic bactericide would be too small to provide a satisfactory bactericidal effect whereas more than 0.2% would cause stimulation or pungency and a peculiar taste or smell to the oral cavity.

The oil-soluble flavors which can be extracted with an aqueous ethanol solution include (1) essential oils such as peppermint oil, spearmint oil, anis oil, allspice oil, Cardamom oil, Cassia oil, Cinnamon oil, Citrus oil, Clove oil, Coriander oil, Eucalyptus oil, Fennel oil, Nutmeg oil, Perilla oil, Lavender oil, Lavandin oil, Wintergreen oil and the like, (2) flavor compounds such as fruit flavor (e.g., strawberry, banana, melon, fruitmix, citrus, pineapple, tutti fruit, cherry, apple, peach, grape, etc.), floral flavor (e.g., carnation, hyacinth, gardenia, lily of the valley, lilac, Jasmine, rose, violet, etc.) and the like, (3) flavor chemicals such as limonene, cineole, menthol, linalool, anethole, eugenol, menthone, carvone, methyl salicylate, cinnamic aldehyde and the like.

They are used alone or in admixture of two or more.

The water-soluble flavor blended in the inventive composition is obtained by adding the above-mentioned oil-soluble flavor to an aqueous ethanol solution, mixing them for extraction, and collecting a lower layer therefrom. The aqueous ethanol solution and the oil-soluble flavor are preferably mixed such that there is 0.1 to 10 parts, more preferably 0.2 to 3 parts by weight of the oil-soluble flavor per part by weight of the aqueous ethanol solution. On this basis, less than 0.1 part of the oil-soluble flavor would be too small for definite separation of the two phases or if separation is possible, the lower layer separated therefrom would be less effective for masking a peculiar taste when blended in the oral composition. If the amount of the oil-soluble flavor exceeds 10 parts, the lower layer separated therefrom would create insoluble matter or cause liquid separation when blended in the oral composition.

Desirably the aqueous ethanol solution used herein is a mixture of ethanol and water in a weight ratio between 8:2 and 2:8, especially between 6:4 and 4:6. An aqueous ethanol solution having a higher ethanol concentration outside the range would not separate into two layers when mixed with the oil-soluble flavor. If such a mixture is blended in the oral composition, storage stability would be exacerbated or the peculiar taste would not be masked. An aqueous ethanol solution having a lower ethanol concentration outside the range would not be effective for masking the peculiar taste although storage stability is acceptable.

Preferably the water-soluble flavor is blended in an amount of about 0.01 to about 2% by weight, more preferably about 0.1 to about 1% by weight of the entire composition. Less than 0.01% of the water-soluble flavor would be too small to mask the peculiar taste of the cationic bactericide whereas more than 2% of the water-soluble flavor would render the composition unstable during storage.

Also blended in the oral composition is cyclodextrin. Examples of cyclodextrin include α-, β-, γ-, branched type, and chemically modified type cyclodextrins.

Preferably cyclodextrin is blended in an amount of about 0.002 to about 10% by weight, more preferably about 0.01 to about 5% by weight of the entire composition. Less than 0.002% of cyclodextrin would not be effective for improving storage stability whereas more than 10% would be less desirable when the cost of a product is taken into account.

In addition to the water-soluble flavor, any commonly used oil-soluble flavor may be added to the inventive composition insofar as the benefits of the invention are not lost. Where the composition contains cyclodextrin, an oil-soluble flavor can be added in conventional amounts because the cyclodextrin is also effective for solubilizing the oil-soluble flavor.

In addition to the essential components mentioned above, the oral composition of the invention may contain any of other active ingredients including organic acids or organic acid salts such as tranexamic acid and glycyrrhizin salts; enzymes such as dextranase, amylase, protease, mutanase, lysozyme, and lytic enzyme; alkali metal monofluorophosphates such as sodium monofluorophosphate; fluorides and stannous compounds such as sodium fluoride and stannous fluoride; epsilon-aminocaproic acid, aluminum chlorohydroxyallantoin, dihydro-cholesterol, sodium chloride, water-soluble phosphoric acid compounds such as potassium and sodium salts of ortho-phosphoric acid, azulene, and vitamins, alone or in admixture of two or more. These active ingredients may be added in conventional amounts insofar as the benefits of the invention are not lost.

Any of other components commonly used may be blended in the inventive composition in accordance with a particular type thereof and the resulting mixture may be conventionally processed into the desired type of preparation. In preparing a mouthwash, for example, a humectant, sweetener, pH adjusting agent, preservative, solvent and the like are used. The humectant used herein includes sorbitol, glycerin, propylene glycol, 1,3-butylene glycol, polyoxyethylene glycol, xylitol, maltitol, and lactitol alone or in admixture. The sweetener used herein includes stevioside, stevia extract, levaudioside, neohesperidyl dihydrochalcone, acesulfam, taumatine, glycyrrhizin, glycyrrhizin monogluconide, hernandulcin, perillartine, saccharin, saccharin sodium, alone or in admixture. The pH adjusting agent used herein includes organic acids and salts thereof such as citric acid and its salts, phosphoric acid and its salts, malic acid and its salts, and acetic acid and its salts, alone or in admixture. Methylparaben is an exemplary preservative. Ethanol and water are exemplary solvents. These and other ingredients are blended and mixed to prepare a mouthwash. Other types of oral compositions may be prepared in a conventional manner using appropriate ingredients selected for a particular type.

The thus obtained oral composition is on use after it is filled in appropriate containers, for example, such as aluminum tubes, laminate tubes having aluminum foil laminated with plastic material on either surface, plastic tubes, bottles and aerosol containers.

There has been described an oral composition containing a cationic bactericide which allows the cationic bactericide to exert its activity to a full extent, which is effective for masking the peculiar taste inherent to the cationic bactericide and thus presents no peculiar taste, but a pleasant feel on use, and which is stable during shelf storage. The composition finds a variety of applications.

EXAMPLE

Examples of the present invention are given below together with Tests by way of illustration and not by way of limitation. All percents are by weight.

Test 1

The influence on the activity of a cationic bactericide by anionic and nonionic surfactants blended therewith was determined by the following test.

Test method (method for measuring minimum growth inhibiting concentration by dilution)

1. A given amount of sterilized hydroxyapatite beads (manufactured by BDH Co.) were coated with sterilized saliva and then washed with sterilized phosphate buffered saline (PBS).
2. The washed hydroxyapatite beads were immersed for reaction in a solution of the following formulation at room temperature for 30 minutes.

| Solution formulation | |
|---|---|
| Cationic bactericide (benzalkonium chloride) | 0.05% |
| Surfactant shown in Table 1 | 1.5% |
| Water | balance |
| | 100.0% |

3. At the end of reaction, the solution was removed and the beads were washed with PBS, and a THB medium (TODD HEWITT broth medium manufactured by DIFCO) was added thereto.
4. From the medium together with the hydroxyapatite beads, a series of dilutions were prepared by varying the dilution concentration by a factor of 2n. Each dilution was incubated with a predetermined amount of an *Actinomyces viscosus* T14V strain and anaerobic cultivation done at 37° C. for 24 hours.
5. Growth of bacteria was judged by visually observing the turbidity of the medium, determining the minimum growth inhibiting concentration (MIC) from the dilution factor.

The control used was an aqueous solution of the cationic bactericide (benzalkonium chloride) without a surfactant. The bactericidal activity of the solutions was rated according to the following criterion.

Antibacterial Activity (titer) Ratings

○: an approximately equal MIC to Control
Δ: MIC corresponding to less than ⅛ of Control
×: MIC corresponding to less than 1/32 of Control

TABLE 1

| Surfactant | Antibacterial activity rating |
|---|---|
| Control (no surfactant) | ○ |
| Sodium lauryl sulfate | × |
| Lauroyl sarcosinate | × |
| α-olefin sulfonate | × |
| Lauryl monoglyceride sulfate | × |
| Lauryl monoglyceride sulfonate | × |
| Lauroyl diethanol amide | × |
| Stearyl monoglyceride | × |
| Polyoxyethylene hardened castor oil | × |
| POE—POP block copolymer | × or Δ |
| Sucrose fatty acid ester | × or Δ |
| PolySolvate 80 | × |
| Sorbitan monostearate | × |

It is seen from Table 1 that when anionic and nonionic surfactants having solubilizing ability commonly used in conventional oral compositions are blended, the cationic bactericide is drastically reduced in activity. Equivalent activity to the surfactant-free composition can be achieved, but with difficulty, by increasing the amount of bactericide blended or by using a small amount of a less activity dropping surfactant. The former approach causes oral mucosa stripping and oral stimulation. The latter approach would yet be accompanied by an activity lowering and would fail to mask the peculiar taste inherent to the selected surfactant and the peculiar taste of the base substance and the bactericide, and thus present an unpleasant feel on use. It is very difficult to find a compromise between storage stability and masking of a peculiar taste.

Test 2

Liquid mouth refreshers of the formulation shown in Tables 2 and 3 were prepared wherein a cationic bactericide was used in combination with a water-soluble flavor as shown in Table 3. The samples were evaluated for bactericidal activity, masking of a peculiar taste and storage stability in accordance with the following criterion.

Antibacterial Activity

○: equivalent to a sample free of a surfactant having solubilizing ability
Δ: activity corresponding to less than ⅛ of "○" rated sample
×: activity corresponding to less than 1/32 of "○" rated sample Masking of a Peculiar Taste A specialized panel of ten persons rated a sample on a 5-point scale and a weighted average was calculated therefrom.

○: more than 4 points on average
Δ: more than 3 points on average
×: less than 3 points on average Outer Appearance Stability ○: clear
Δ: somewhat turbid
×: turbid

TABLE 2

| Formulation (%) | No. 1 | No. 2 | No. 3 | No. 4 | No. 5 | No. 6 | No. 7 | No. 8 |
|---|---|---|---|---|---|---|---|---|
| Ethanol (95%) | 15.0 | 15.0 | 15.0 | 15.0 | 15.0 | 15.0 | 15.0 | 15.0 |
| Glycerin (85%) | 10.0 | 10.0 | 10.0 | 10.0 | 10.0 | 10.0 | 10.0 | 10.0 |
| Benzalkonium chloride | 0.05 | 0.05 | 0.05 | 0.05 | 0.05 | 0.05 | 0.05 | 0.05 |
| Water-soluble flavor (A to H)* | A1.00 | B1.00 | C1.00 | D1.00 | E1.00 | F1.00 | G1.00 | H1.00 |
| Water | balance | balance | balance | balance | balance | balance | balance | balance |
| Total | 100.0 | 100.0 | 100.0 | 100.0 | 100.0 | 100.0 | 100.0 | 100.0 |
| Bactericidal activity | ○ | ○ | ○ | ○ | ○ | ○ | ○ | ○ |
| Peculiar taste masking | Δ or × | Δ or × | ○ or Δ | ○ | ○ | ○ | ○ Δ | Δ or × |

TABLE 2-continued

| Formulation (%) | No. 1 | No. 2 | No. 3 | No. 4 | No. 5 | No. 6 | No. 7 | No. 8 |
|---|---|---|---|---|---|---|---|---|
| Outside appearance stability | × | × | ○ | ○ | ○ | ○ or Δ | Δ or × | × |
| Total rating | × | × | ○ | ○ | ○ | ○ | × | × |

TABLE 3

| Formulation (%) | No. 1 | No. 2 | No. 3 | No. 4 | No. 5 | No. 6 | No. 7 | No. 8 |
|---|---|---|---|---|---|---|---|---|
| Ethanol (95%) | 15.0 | 15.0 | 15.0 | 15.0 | 15.0 | 15.0 | 15.0 | 15.0 |
| Glycerin (85%) | 10.0 | 10.0 | 10.0 | 10.0 | 10.0 | 10.0 | 10.0 | 10.0 |
| Chlorhexidine gluconate | 0.05 | 0.05 | 0.05 | 0.05 | 0.05 | 0.05 | 0.05 | 0.05 |
| Water-soluble flavor (A to H)* | A1.00 | B1.00 | C1.00 | D1.00 | E1.00 | F1.00 | G1.00 | H1.00 |
| Water | balance | balance | balance | balance | balance | balance | balance | balance |
| Total | 100.0 | 100.0 | 100.0 | 100.0 | 100.0 | 100.0 | 100.0 | 100.0 |
| Bactericidal activity | ○ | ○ | ○ | ○ | ○ | ○ | ○ | ○ |
| Peculiar taste masking | × | Δ or × | Δ | ○ | ○ | ○ | Δ | × |
| Outside appearance stability | × | × | ○ | ○ | ○ | ○ or Δ | Δ or × | × |
| Total rating | × | × | ○ | ○ | ○ | ○ | × | × |

*The water-soluble flavor was a lower layer fraction obtained by extracting an oil-soluble flavor with an aqueous ethanol solution as shown in Table 4.

TABLE 4

| Water-soluble flavor composition (%) | A | B | C | D | E | F | G | H |
|---|---|---|---|---|---|---|---|---|
| Ethanol | 95.0 | 90.0 | 80.0 | 60.0 | 40.0 | 20.0 | 10.0 | 5.0 |
| Water | 5.0 | 10.0 | 20.0 | 40.0 | 60.0 | 80.0 | 90.0 | 95.0 |
| Oil-soluble flavor** | 100.0 | 100.0 | 100.0 | 100.0 | 100.0 | 100.0 | 100.0 | 100.0 |
| Total | 200.0 | 200.0 | 200.0 | 200.0 | 200.0 | 200.0 | 200.0 | 200.0 |

**Oil-soluble flavor

| peppermint oil | 50.0% |
|---|---|
| fruit flavor | 25.0% |
| coriander oil | 2.5% |
| glycerin | 22.5% |
| Total | 100.0% |

It is seen from Tables 2 and 3 that when a water-soluble flavor obtained by extracting an oil-soluble flavor with an aqueous ethanol solution is added to an oral composition containing a cationic bactericide, there are obtained advantages including high bactericidal activity, masking of a peculiar taste, and improved storage stability.

Test 3

Liquid mouth refreshers of the formulation shown in Tables 5 and 6 were prepared wherein a cationic bactericide was used in combination with α-cyclodextrin. The samples were evaluated for bactericidal activity, masking of a peculiar taste and storage stability in accordance with the same criterion as in Test 2.

TABLE 5

| Formulation (%) | No. 9 | No. 10 | No. 11 | No. 12 | No. 13 | No. 14 |
|---|---|---|---|---|---|---|
| Ethanol (95%) | 15.0 | 15.0 | 15.0 | 15.0 | 15.0 | 15.0 |
| Glycerin (85%) | 10.0 | 10.0 | 10.0 | 10.0 | 10.0 | 10.0 |
| Benzalkonium chloride | 0.05 | 0.05 | 0.05 | 0.05 | 0.05 | 0.05 |
| Oil-soluble flavor** | 0.03 | 0.05 | 0.02 | 0.01 | 0.03 | 0.03 |
| α-cyclodextrin | 0.01 | 0.02 | 0.05 | 0.10 | 1.00 | 5.00 |
| Water | balance | balance | balance | balance | balance | balance |
| Total | 100.0 | 100.0 | 100.0 | 100.0 | 100.0 | 100.0 |
| Bactericidal activity | ○ | ○ | ○ | ○ | ○ | ○ |
| Peculiar taste masking | ○ | ○ | ○ | ○ | ○ or Δ | Δ or × |
| Outside appearance stability | ○ or Δ | ○ | ○ | ○ | ○ | ○ or Δ |
| Total rating | ○ | ○ | ○ | ○ | ○ | Δ |

TABLE 6

| Formulation (%) | No. 9 | No. 10 | No. 11 | No. 12 | No. 13 | No. 14 |
|---|---|---|---|---|---|---|
| Ethanol (95%) | 15.0 | 15.0 | 15.0 | 15.0 | 15.0 | 15.0 |
| Glycerin (85%) | 10.0 | 10.0 | 10.0 | 10.0 | 10.0 | 10.0 |
| Chlorhexidien gluconate | 0.05 | 0.05 | 0.05 | 0.05 | 0.05 | 0.05 |
| Oil-soluble flavor** | 0.03 | 0.05 | 0.02 | 0.01 | 0.03 | 0.03 |
| α-cyclodextrin | 0.01 | 0.02 | 0.05 | 0.10 | 1.00 | 5.00 |
| Water | balance | balance | balance | balance | balance | balance |
| Total | 100.0 | 100.0 | 100.0 | 100.0 | 100.0 | 100.0 |
| Bactericidal activity | ○ | ○ | ○ | ○ | ○ | ○ |
| Peculiar taste masking | Δ | ○ | ○ | ○ | Δ | Δ or × |
| Outside appearance stability | ○ or Δ | ○ | ○ | ○ | ○ | ○ or Δ |
| Total rating | ○ | ○ | ○ | ○ | ○ | Δ |

**The oil-soluble flavor was of the same composition as used in the extraction of the water-soluble flavor (see Table 4).

It is seen from Tables 5 and 6 that when α-cyclodextrin is added to an oral composition containing a cationic bactericide, the oil-soluble flavor is solubilized without blending a surfactant having solubilizing ability and there are obtained advantages including high bactericidal activity, masking of a peculiar taste, and improved storage stability.

Test 4

Liquid mouth refreshers of the formulation shown in Tables 7 and 8 were prepared wherein a cationic bactericide was used in combination with a water-soluble flavor and α-cyclodextrin. The samples were evaluated for bactericidal activity, masking of a peculiar taste and storage stability in accordance with the same criterion as in Test 2.

TABLE 7

| Formulation (%) | No. 15 | No. 16 | No. 17 | No. 18 | No. 19 | No. 20 |
|---|---|---|---|---|---|---|
| Ethanol (95%) | 15.0 | 15.0 | 15.0 | 15.0 | 15.0 | 15.0 |
| Glycerin (85%) | 10.0 | 10.0 | 10.0 | 10.0 | 10.0 | 10.0 |
| Benzalkonium chloride | 0.05 | 0.05 | 0.05 | 0.05 | 0.05 | 0.05 |
| Water-soluble flavor*** | 0.50 | 0.50 | 0.50 | 0.50 | 0.50 | 0.50 |
| α-cyclodextrin | 0.005 | 0.01 | 0.02 | 0.05 | 1.10 | 1.00 |
| Water | balance | balance | balance | balance | balance | balance |
| Total | 100.0 | 100.0 | 100.0 | 100.0 | 100.0 | 100.0 |
| Bactericidal activity | ○ | ○ | ○ | ○ | ○ | ○ |
| Peculiar taste masking | ○ | ○ | ○ | ○ | ○ | ○ or Δ |
| Outside appearance stability | ○ or Δ | ○ | ○ | ○ | ○ | ○ |
| Total rating | ○ | ○ | ○ | ○ | ○ | ○ |

TABLE 8

| Formulation (%) | No. 15 | No. 16 | No. 17 | No. 18 | No. 19 | No. 20 |
|---|---|---|---|---|---|---|
| Ethanol (95%) | 15.0 | 15.0 | 15.0 | 15.0 | 15.0 | 15.0 |
| Glycerin (85%) | 10.0 | 10.0 | 10.0 | 10.0 | 10.0 | 10.0 |
| Chlorhexidine gluconate | 0.05 | 0.05 | 0.05 | 0.05 | 0.05 | 0.05 |
| Water-soluble flavor*** | 0.50 | 0.50 | 0.50 | 0.50 | 0.50 | 0.50 |
| α-cyclodextrin | 0.005 | 0.01 | 0.02 | 0.05 | 1.10 | 1.00 |
| Water | balance | balance | balance | balance | balance | balance |
| Total | 100.0 | 100.0 | 100.0 | 100.0 | 100.0 | 100.0 |
| Bactericidal activity | ○ | ○ | ○ | ○ | ○ | ○ |
| Peculiar taste masking | ○ | ○ | ○ | ○ | ○ | ○ or Δ |
| Outside appearance stability | ○ or Δ | ○ | ○ | ○ | ○ | ○ |
| Total rating | ○ | ○ | ○ | ○ | ○ | ○ |

***The water-soluble flavor was a lower layer fraction obtained by extracting an oil-soluble flavor with an aqueous ethanol solution as follows.

| | |
|---|---|
| Ethanol | 25% |
| Water | 25% |
| Oil-soluble flavor (see Table 4) | 50% |
| Total | 100.0% |

It is seen from Tables 7 and 8 that when a water-soluble flavor and cyclodextrin are added to an oral composition containing a cationic bactericide, but free of a surfactant having solubilizing ability, masking of a peculiar taste and storage stability are achieved at no sacrifice of bactericidal activity.

Example 1: Dental rinse

| | |
|---|---|
| Chlorhexidine gluconate | 0.05 |
| Triclosan | 0.005 |
| Xylitol | 15.0 |
| Taumatine | 0.05 |
| Glycyrrhizin monogluconide | 0.003 |
| Branched cyclodextrin | 0.03 |
| Menthol | 0.01 |
| Strawberry flavor | 0.005 |
| Ethanol | 5.0 |
| Pure water | Balance |
| Total | 100.0% |

Example 2: Mouthwash

| | |
|---|---|
| Benzethonium chloride | 0.05 |
| Sodium fluoride | 0.05 |
| Sorbitol (65%) | 20.0 |
| Acesulfam | 0.005 |
| Methylparaben | 0.01 |
| β-cyclodextrin | 0.01 |
| Water-soluble spearmint oil 1) | 0.5 |
| Menthol | 0.05 |
| Methyl salicylate | 0.005 |
| Water-soluble spice mix oil 2) | 0.05 |
| Ethanol | 15.0 |
| Pure water | Balance |
| Total | 100.0% |

Example 3: Mouthwash

| | |
|---|---|
| Cetyl pyridinium chloride | 0.05 |
| Tranexamic acid | 0.05 |
| Glycerin (85%) | 9.0 |
| Hemandulcin | 0.05 |
| Citric acid | 0.05 |
| Sodium citrate | 0.3 |
| Water-soluble peppermint oil 3) | 0.5 |
| Menthol | 0.01 |
| Ethanol | 15.0 |
| Pure water | Balance |
| Total | 100.0% |

Example 4: Liquid mouth refresher

| | |
|---|---|
| Chlorhexidine gluconate | 0.02 |
| Triclosan | 0.005 |
| Glycerin (85%) | 15.0 |
| Hemandulcin | 0.05 |
| Perillartine | 0.05 |
| Vitamin C | 0.003 |
| Modified cyclodextrin | 0.03 |
| Menthol | 0.20 |
| Water-soluble fruit flavor 4) | 0.5 |
| Anethol | 0.003 |
| Ethanol | 50.0 |
| Pure water | Balance |
| Total | 100.0% |

Example 5: Troche

| | |
|---|---|
| Gum arabic | 7.0 |
| Glucose | 80.0 |
| Gelatin | 4.0 |
| Benzethonium chloride | 0.05 |
| Lysozyme chloride | 0.05 |
| Citric acid | 0.05 |
| Sodium acetate | 5.0 |
| Water-soluble strawberry oil 5) | 1.0 |
| Pure water | Balance |
| Total | 100.0% |

Example 6: Toothpaste

| | |
|---|---|
| Benzalkonium chloride | 0.05 |
| Triclosan | 0.005 |
| Sodium fluoride | 0.005 |
| Calcium carbonate | 50.0 |
| Carrageenan | 0.6 |
| Sodium carboxymethyl cellulose | 0.5 |
| Glycerin (85%) | 20.0 |
| Vitamin E | 0.003 |
| Sodium chloride | 0.5 |
| Menthol | 0.50 |
| Water-soluble herb oil 6) | 0.50 |
| Anethole | 0.1 |
| Spicemix flavor | 0.001 |
| Spilanthol | 0.003 |
| Pure water | Balance |
| Total | 100.0% |

Example 7: Toothpaste

| | |
|---|---|
| Chlorhexidine hydrochloride | 0.02 |
| Cetylpyridinium bromide | 0.05 |
| Stannous fluoride | 0.005 |
| Azulene | 0.001 |
| Calcium hydrogen phosphate dihydrate | 50.0 |
| Carrageenan | 0.8 |
| Sodium carboxymethyl cellulose | 0.6 |
| Sorbitol (60%) | 25.0 |
| Propylparaben | 0.01 |
| Menthol | 0.30 |
| Water-soluble floral flavor 7) | 0.50 |
| Water-soluble star anise flavor 8) | 0.3 |
| Peppermint oil | 0.02 |
| γ-cyclodextrin | 0.02 |
| Pure water | Balance |
| Total | 100.0% |

Example 8: Liquid dentifrice

| | |
|---|---|
| Benzalkonium chloride | 0.05 |
| Triclosan | 0.05 |
| Dextranase | 200 U/g |
| Silicic anhydride | 30.0 |
| Glycerin (85%) | 35.0 |
| Propylene glycol | 5.0 |
| Menthol | 0.50 |
| Water-soluble citrus oil 9) | 0.50 |
| Eucalyptus oil | 0.1 |
| Clove oil | 0.002 |
| Ethanol | 2.5 |
| Dye | trace |
| Pure water | Balance |
| Total | 100.0% |

1) A lower layer fraction obtained by extracting spearmint oil with aqueous ethanol (ethanol to water ratio 5:5).
2) A lower layer fraction obtained by extracting spice mix oil with aqueous ethanol (ethanol to water ratio 4:6).
3) A lower layer fraction obtained by extracting peppermint oil with aqueous ethanol (ethanol to water ratio 6:4).
4) A lower layer fraction obtained by extracting fruit flavor oil with aqueous ethanol (ethanol to water ratio 7:3).
5) A lower layer fraction obtained by extracting strawberry oil with aqueous ethanol (ethanol to water ratio 7:3).
6) A lower layer fraction obtained by extracting herb oil with aqueous ethanol (ethanol to water ratio 4:6).
7) A lower layer fraction obtained by extracting floral flavor with aqueous ethanol (ethanol to water ratio 4:6).

-continued

8) A lower layer fraction obtained by extracting star anise flavor with aqueous ethanol (ethanol to water ratio 8:2).
9) A lower layer fraction obtained by extracting citrus oil with aqueous ethanol (ethanol to water ratio 4:6).

Japanese Patent Application No. 5-220646 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

I claim:

1. An oral composition comprising:
   a cationic bactericide and
   a water-soluble flavor obtained by extracting an oil-soluble flavor with an aqueous ethanol solution:
   the composition being free of anionic and nonionic surfactants.

2. The oral composition of claim 1 wherein the aqueous ethanol solution contains ethanol and water in a weight ratio between 8:2 and 2:8.

3. An oral composition comprising a cationic bactericide and a water-soluble flavor obtained by adding 0.1 to 10 parts by weight of an oil-soluble flavor to 1 part of an aqueous ethanol solution containing ethanol and water in a weight ratio between 8:2 and 2:8, mixing them for extraction, and collecting a lower layer therefrom,
   the composition being free of anionic and nonionic surfactants.

4. The oral composition of claim 3 wherein the oil soluble flavor is selected from the group consisting of peppermint oil, spearmint oil, anis oil, allspice oil, Cardamom oil, Cassia oil, Cinnamon oil, Citrus oil, Clove oil, Coriander oil, Eucalyptus oil, Fennel oil, Nutmeg oil, Perilla oil, Lavender oil, Lavandin oil, Wintergreen oil, fruit flavor (e.g., strawberry, banana, melon, fruitmix, citrus, pineapple, tutti fruit, cherry, apple, peach, grape, etc.), floral flavor (e.g., carnation, hyacinth, gardenia, lily of the valley, lilac, Jasmine, rose, violet, etc.), limonene, cineole, menthol, linalool, anethole, eugenol, menthone, carvone, methyl salicylate, and cinnamic aldehyde.

5. An oral composition comprising a cationic bactericide, a cyclodextrin and a water-soluble flavor obtained by adding 0.1 to 10 parts by weight of an oil-soluble flavor to 1 part of an aqueous ethanol solution containing ethanol and water in a weight ratio between 8:2 and 2:8, mixing them for extraction, and collecting a lower layer therefrom,
   the composition being free of anionic and nonionic surfactants.

6. The oral composition of claim 5 wherein the oil soluble flavor is selected from the group consisting of peppermint oil, spearmint oil, anis oil, allspice oil, Cardamom oil, Cassia oil, Cinnamon oil, Citrus oil, Clove oil, Coriander oil, Eucalyptus oil, Fennel oil, Nutmeg oil, Perilla oil, Lavender oil, Lavandin oil, Wintergreen oil, fruit flavor (e.g., strawberry, banana, melon, fruitmix, citrus, pineapple, tutti fruit, cherry, apple, peach, grape, etc.), floral flavor (e.g., carnation, hyacinth, gardenia, lily of the valley, lilac, Jasmine, rose, violet, etc.), limonene, cineole, menthol, linalool, anethole, eugenol, menthone, carvone, methyl salicylate, and cinnamic aldehyde.

\* \* \* \* \*